United States Patent [19]
Capuder

[11] Patent Number: 6,127,358
[45] Date of Patent: *Oct. 3, 2000

[54] ISOLATION OF CLAVULANIC ACID FROM FERMENTATION BROTH BY ULTRAFILTRATION

[75] Inventor: Egidij Capuder, Krtina, Slovenia

[73] Assignee: Urquhart-Dykes & Lord, Leeds, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/000,375

[22] PCT Filed: Aug. 27, 1996

[86] PCT No.: PCT/GB96/02083

§ 371 Date: Jun. 1, 1998

§ 102(e) Date: Jun. 1, 1998

[87] PCT Pub. No.: WO97/08175

PCT Pub. Date: Mar. 6, 1997

[30] Foreign Application Priority Data

Aug. 28, 1995 [SI] Slovenia ................. 9500265

[51] Int. Cl.$^7$ .......................... A01N 43/00; C07D 487/08
[52] U.S. Cl. ............................. 514/210; 540/348
[58] Field of Search ............................ 540/348; 514/210

[56] References Cited

U.S. PATENT DOCUMENTS

| | | | |
|---|---|---|---|
| 3,873,425 | 3/1975 | Kobayashi et al. | 195/36 |
| 4,072,569 | 2/1978 | Box | 195/80 |
| 4,140,764 | 2/1979 | Howarth | 424/114 |
| 4,148,880 | 4/1979 | Celmer et al. | 424/119 |
| 4,427,690 | 1/1984 | Cole et al. | 424/272 |
| 4,525,353 | 6/1985 | Cole et al. | 424/114 |
| 4,886,602 | 12/1989 | Kuehne | 210/637 |
| 4,956,180 | 9/1990 | Cassani et al. | 424/118 |
| 5,268,283 | 12/1993 | Mothes et al. | 435/144 |
| 5,310,898 | 5/1994 | Copar | 540/349 |
| 5,422,256 | 6/1995 | Cooper et al. | 435/128 |

FOREIGN PATENT DOCUMENTS

| | | |
|---|---|---|
| 400 846 | 8/1995 | Austria . |
| 0182522 | 5/1986 | European Pat. Off. . |
| 0385552 | 9/1990 | European Pat. Off. . |
| 0391590 | 10/1990 | European Pat. Off. . |
| 0 431 679 B1 | 10/1994 | European Pat. Off. . |
| 0714884 | 6/1996 | European Pat. Off. . |
| 0 811 689 A1 | 10/1997 | European Pat. Off. . |
| 60-70092 | 4/1985 | Japan . |
| 4-75595 | 10/1992 | Japan . |
| 172021 | 12/1993 | Poland . |
| 1508977 | 4/1978 | United Kingdom . |
| 1 578 739 | 5/1980 | United Kingdom . |
| 1 563 103 | 9/1980 | United Kingdom . |
| 2088378 | 6/1982 | United Kingdom . |
| WO94/22873 | 10/1994 | WIPO . |
| WO9511295 | 4/1995 | WIPO . |
| 95/23870 | 9/1995 | WIPO . |
| WO9523870 | 9/1995 | WIPO . |
| WO96/28452 | 9/1996 | WIPO . |
| 96/33197 | 10/1996 | WIPO . |
| WO96/33197 | 10/1996 | WIPO . |

OTHER PUBLICATIONS

Belter, et al., Bioseparations: Downstream Processing for Biotechnology, John Wiley & Sons, New York, 1988, Chapter 2 "Filtration and Microfilitration," pp. 13–17, 39–42, and Chapter 9 "Ultrafiltration and Electrophoresis," pp. 237–238, 250–255.

Noble, et al., Membrane Separations Technology: Principles and Applications, Elsevier, 1995, Chapter 8 "Membrane Bioseparations," pp. 353–413.

Melling, "Applications of Ultrafiltration–Modifying Factors," Process Biochem, 1974, Sep. (7), pp. 7–10.

Kalyanpur, et al., Chapter 32 Isolation of Cephalosporin C from Fermentation Broths Using Membrane Systems and High–Performance Liquid Chromatography, Dev. Ind. Microbiol., 1985, 26, pp. 455–470.

Kalyanpur, et al., "Isolation of Cephalosporin C from Fermentation Broths Using Membrane Systems and HPLC," ChemSA, 1984, SA Filtration, Nov., pp. 8–12.

Michaels, et al., "Membranes in Biotechnology: State of Art," Desalination, vol. 53, pp. 231–258, (1985).

Denis Butterworth, "Clavulanic Acid: Properties, Biosynthesis, and Fermentation"., vol. 22, pp. 225–235, (1984).

Ullmann's Encyclopedia of Industrial Chemistry, VCH Publishers, 1990, vol. 16., pp.194–195.

A.M.A. Nabais et al., "Ultrafiltration of fermented broths and solvent extraction of antibiotics", Bioprocess Engineering, vol. 13, pp. 215–221, 1995.

Mackay and Salusbury, "Choosing between centrifugation and crossflow microfiltration ", The Chemical Engineer, Apr. 1988, pp. 45–50.

*Primary Examiner*—Mukund J. Shah
*Assistant Examiner*—Tamthom N. Truong
*Attorney, Agent, or Firm*—Beyer Weaver & Thomas, LLP.

[57] ABSTRACT

Provided is a process for preparation and/or purification of clavulanic acid or a pharmaceutically acceptable salt or ester thereof including removing solids from a clavulanic acid containing fermentation broth by microfiltration to form a first filtrate, further removing solids from the first filtrate by ultrafiltration to form a second filtrate, concentrating the second filtrate by removal of water, and treating the concentrated second filtrate to isolate clavulanic acid or a pharmaceutically acceptable salt or ester thereof, characterized in that the first filtrate is filtered using an ultrafiltration membrane having a molecular weight cut-off of 10 to 30 kD and a permeate flow rate of 10 to 30 $lm^{-2} h^{-1}$.

9 Claims, No Drawings

ISOLATION OF CLAVULANIC ACID FROM FERMENTATION BROTH BY ULTRAFILTRATION

This invention relates to a process for purification and/or preparation of clavulanic acid and pharmaceutically acceptable salts and esters of clavulanic acid, particularly but not exclusively alkali salts especially potassium clavulanate.

Clavulanic acid is the common name for (2R,5R,Z)-30 (2-hydroxyethylidene)-7-oxo-4-oxa-1-azabicyclo [3.2.0] heptane-2-carboxylic acid. Clavulanic acid and its alkali metal salts and esters are active as inhibitors of beta lactamase produced by some Gram positive as well as Gram negative micro-organisms. In addition to inhibition of beta lactamase, clavulanic acid and alkali metal salts thereof also have a synergistic action with penicillin and cephalosporin antibiotics. Clavulanic acid and its salts are used in pharmaceutical preparations to prevent the deactivation of beta lactam antibiotics. Commercial preparations contain potassium clavulanate in combination with amoxycillin trihydrate. Potassium clavulanate is more stable than the free acid or other salts.

Clavulanic acid is prepared by fermentation of a microorganism such as strains of Streptomyces such as *S.clavuligerus* NRRL 3585, *S.jumonjinensis* NRRL 5741 and *S.katsurahamanus* IFO 13716 and Streptomyces sp.P6621 FERM P2804. The aqueous culture obtained after fermentation is purified and concentrated in accordance with conventional processes for example filtration and chromatographic purification as disclosed in GB 1508977, prior to extraction of the aqueous solution with an organic solvent to obtain a solution of impure clavulanic acid in the solvent.

GB 1508977 discloses preparation of clavulanate salts by filtration of the fermentation broth by passage through an anionic exchange resin. This process may achieve acceptable yields but sophisticated chromatographic purification methods are required and the use of resin columns involves substantial investment for manufacture on a commercial scale.

GB 1543563 discloses a fermentation process wherein the pH value of the medium is maintained in the range 6.3 to 6.7. Pharmaceutically acceptable salts such as potassium clavulanate are prepared by re-salting from lithium clavulanate.

EP-A-0026044 discloses use of the tertiary butylamine salt of clavulanic acid as an intermediate for purification of clavulanic acid. This salt was known from BE-862211 or DE 2733230 which disclosed that the salt was even more stable than the sodium or potassium clavulanate salts. Tertiary butylamine is a toxic compound and is also difficult to remove from waste water giving rise to serious pollution concerns.

EP-A-0562583 discloses use of salts of clavulanic acid with N,N'-monosubstituted symmetric ethylene diamines such as N,N'-diisopropylethylene diammonium diclavulanate as useful intermediates for isolation and preparation of pure clavulanic acid or alkaline metal clavulanate salts from ethyl acetate extract.

Conventionally filtered clavulanic acid containing fermentation broths may contain 10 to 20% of proteins calculated on the amount of clavulanic acid. These proteins hinder the subsequent isolation and purification of the clavulanic acid. Treatment of the filtered broth with ion exchange resins or flocculants is time consuming, expensive and can enhance the degradation of the unstable product.

According to the present invention a process for preparation and/or purification of clavulanic acid or a pharmaceutically acceptable salt or ester thereof comprises the steps of:

removing solids from a clavulanic acid containing fermentation broth by microfiltration to form a first filtrate, further removing solids from the first filtrate by ultrafiltration to form a second filtrate, concentrating the second filtrate by removal of water, and treating the concentrated second filtrate to isolate clavulanic acid or a pharmaceutically acceptable salt or ester thereof characterised in that the first filtrate is filtered using an ultrafiltration membrane having a molecular weight cut-off of 10 to 30 kD and a permeate flow rate of 10 to 30 $lm^{-2} h^{-1}$.

Use of ultrafiltration in accordance with the present invention may afford a sufficiently pure solution of clavulanic acid to avoid any necessity for formation of an intermediate amine or diammonium salt before conversion to potassium clavulanate. Furthermore the second filtrate may be concentrated by reverse osmosis without fouling or formation of an unwanted gel layer on the reverse osmosis membrane surface. The flow rate through the reverse osmosis unit may be improved and the need for frequent cleaning can be avoided.

Use of the present invention has been found to improve the efficiency of isolation of clavulanic acid and has the further advantage that the second filtrate is substantially decoloured by the ultrafiltration step.

Microfiltration of the broth may be carried out as disclosed in our WO95/23870. In a preferred process according to this disclosure the aqueous fermentation broth containing crude clavulanic acid, mycelium, proteins and other suspended solid matter is purified by microfiltration at between pH 5.8 and 6.2 and about 20 to 40° C.

The further treatment of the second filtrate preferably comprises concentration by reverse osmosis. The filtrate may be concentrated to about ⅕ of the original volume to obtain concentrated aqueous clavulanic acid which may be extracted in a series of centrifugal countercurrent extractions with a water immiscible solvent, preferably ethyl acetate, for example as disclosed in WO95/23870.

The extraction is preferably carried out at a temperature between 15 to 25° C. and a pH between 1 and 3. The extract is then dried to a water content below 0.1 vol. % further concentrated by evaporation and decolorised if necessary with active charcoal.

The clavulanic acid in the extract may be reacted with an amine or diamine prior to isolation of the ammonium or diammonium clavulanate salt and conversion of the latter to a pharmaceutically acceptable clavulanate salt or ester. Alternatively the concentrate may be reacted directly with a metal donor to form a pharmaceutically acceptable salt, for example the potassium salt.

The metal donor may be an organic salt, carbonate, bicarbonate or hydroxide of potassium, sodium, lithium or magnesium. Use of an organic salt, preferably a carboxylic acid is preferred. Use of the potassium salt is preferred in view of the comparative stability of potassium clavulanate.

The carboxylic acid may be selected from acetate, propionate, hexanoate, benzoate and benzoate substituted with one or more $C_1$–$C_{10}$ alkyl groups, preferably $C_1$–$C_6$ alkyl groups; halogen; nitro; O, S or NR substituted heteroalkyl; $C_1$–$C_{10}$ alkyl substituted with a group: R, O R, S R, or N $R^1$ $R^2$ wherein R, $R^1$ and $R^2$ are independently $C_1$–$C_{10}$ alkyl.

Preferred metal donors include potassium 2-ethyl hexanoate, potassium acetate, lithium 2-ethyl hexanoate and lithium acetate.

An additional solvent which may comprise a $C_1$–$C_{10}$ alcohol or mixtures thereof may be added. Use of $C_1$–$C_4$ alcohols is preferred. Especially preferred additional solvents include methanol, ethanol, isopropanol and isobutanol and mixtures thereof. Use of isopropanol is especially preferred. These solvents are preferably dry, for example containing between 0% and 4% water. The metal donor may be dissolved in the additional solvent prior to addition to the clavulanic extract. Alternatively the metal donor may be dissolved in the same solvent as the clavulanic acid extract, for example ethyl acetate and the additional solvent added separately.

Particularly advantageous results are obtained when potassium 2-ethyl hexanoate is dissolved in isopropanol, potassium acetate is dissolved in methanol or potassium benzoate is dissolved in methanol. The concentration of the potassium 2-ethyl hexanoate in isopropanol may preferably be 0.1 mol/l to 5 mol/l more advantageously 1 mol/l to 2.5 mol/l and preferably from 1.5 mol/l to 2 mol/l in a 0.8 to 5 molar excess based on the amount of clavulanic acid, preferably in a 5 to 25% molar excess.

The water immiscible solvent used to extract the filtrate of the fermentation broth is preferably selected from ethyl acetate, methyl acetate, propyl acetate, n-butyl acetate, ketones such as methyl ethyl ketone, alcohols such as n-butanol, n-amyl alcohol or halogenated solvents such as methylene chloride chloroform or ethers such as diethyl ether or hexane or mixtures thereof. Use of ethyl acetate is preferred. The concentrate may be purified with activated charcoal and if necessary a silica gel column.

The concentration of crude clavulanic acid in the dried concentrated extract of the water immiscible solvent such as ethyl acetate may be between 8 g/l and 40 g/l preferably between 20 g/l and 40 g/l.

The clavulanate concentrate, preferably in ethyl acetate, may be decolorised by addition of activated charcoal. An amount of 0.2 to 0.5 g of activated charcoal per gram of clavulanic acid has been found to be convenient although alternative amounts may be employed as desired.

The invention is further described by means of example but not in any limitative sense.

EXAMPLE 1

An aqueous filtered broth obtained by fermentation of Streptomyces sp.P6621 FERM P2804 and microfiltration as disclosed in WO95/23870 was used. The microfiltrate permeate had a clavulanic acid content of 3.5 $gl^{-1}$, a protein content of 0.56 $gl^{-1}$, and a light transmittance at 420 nm (after dilution with 1:2 water) of 27.9% was continuously added to a double stepped filtration device type 2NUF2000, manufactured by IMP Promont Ljubljana, Slovenia. The two ultrafiltration washing modules, type GR62-3833/47P made by Filmtech (a subsidiary of the Dow Chemical Co) having two loops with a total membrane area of 194.4 $m^2$. The apparatus was arranged so that the ultrafiltration modules could be connected in parallel or in series. The molecular weight cut-off of the membranes was 20 kD. The filtered broth had a temperature of 35° C., a pH between 5.8 and 6.2 and the permeate flow rate was 12 $lm^{-2} h^{-1}$. The pressure on the membrane was 5 Bar and the longitudinal pressure difference between the concentrate and permeate was 1.4 Bar. The liquids were obtained by ultrafiltration from the first step at a flow rate of 1600 $lh^{-1}$ for the permeate and 400 $lh^{-1}$ for the concentrate. The concentrate from the first ultrafiltration step was used for the second ultrafiltration step and was washed with demineralised water with a flow rate of 800 $lh^{-1}$. The permeate flow rate from the second ultrafiltration step was 800 $lh^{-1}$ and was sent together with permeate from the first loop to the reverse osmosis device.

The clavulanic acid containing permeate was obtained at a flow rate of 2400 $lh^{-1}$ and contained 0.11 $gl^{-1}$ of protein. The light transmittance (420 nm) was 45.1% and the yield was 95% calculated on the assay of clavulanic acid.

I claim:

1. A process for preparation and/or purification of clavulanic acid or a pharmaceutically acceptable salt or ester thereof comprising the steps of:

removing solids from a clavulanic acid containing fermentation broth by microfiltration to form a first filtrate, further removing solids from the first filtrate by ultrafiltration to form a second filtrate, concentrating the second filtrate by removal of water, and treating the concentrated second filtrate to isolate clavulanic acid or a pharmaceutically acceptable salt or ester thereof characterised in that the first filtrate is filtered using an ultrafiltration membrane having a molecular weight cut-off of 10 to 30 kD and a permeate flow rate of 10 to 30 $lm^{-2} h^{-1}$.

2. A process as claimed in claim 1, wherein the pH of the first filtrate before ultrafiltration is 5.8 to 6.2.

3. A process as claimed in claim 1, wherein the ultrafiltration is continuous.

4. A process as claimed in claim 1, wherein continues ultrafiltration is carried out using a double stage apparatus.

5. A process as claimed in claim 1, wherein the ultrafiltration membrane comprises polysulphone.

6. A process as claimed in claim 1, wherein the permeate flow rate is 12 $lm^{-2} h^{-1}$.

7. A process as claimed in claim 1, wherein the molecular weight cut-off is 20 kD.

8. A process for preparation and/or purification of clavulanic acid or a pharmaceutically acceptable salt or ester thereof, characterised in the step of reduction in the quantity of an impurity having an absorbance at 420 nm.

9. A process as claimed in claim 1, wherein said process reduces the quantity of an impurity having an absorbance at about 420 nm.

* * * * *

UNITED STATES PATENT AND TRADEMARK OFFICE
CERTIFICATE OF CORRECTION

PATENT NO.  : 6,127,358
DATED       : October 3, 2000
INVENTOR(S) : Egidij Capuder It is certified that error appears in the above-identified patent and that said Letters Patent are hereby corrected as shown below:

Title page,
    Please replace the Assignee "Urquhart-Dykes & Lord, Leeds, United Kingdom" with --Lek Pharmaceutical & Chemical Co. DD, Ljubljana, Slovenia--.

Signed and Sealed this

Fifteenth Day of May, 2001

*Attest:*

NICHOLAS P. GODICI

*Attesting Officer*      *Acting Director of the United States Patent and Trademark Office*